US008524967B2

(12) United States Patent
Clark et al.

(10) Patent No.: US 8,524,967 B2
(45) Date of Patent: *Sep. 3, 2013

(54) MONOALKYLATED AROMATIC COMPOUND PRODUCTION

(71) Applicant: ExxonMobil Chemical Patents Inc., Baytown, TX (US)

(72) Inventors: Michael C. Clark, Chantilly, VA (US); Frederick Y. Lo, Middlesex, NJ (US); Christine N. Elia, Bridgewater, NJ (US); Yun-Feng Chang, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/676,647

(22) Filed: Nov. 14, 2012

(65) Prior Publication Data

US 2013/0072734 A1 Mar. 21, 2013

Related U.S. Application Data

(63) Continuation of application No. 13/537,811, filed on Jun. 29, 2012, now Pat. No. 8,357,830, which is a continuation of application No. 12/299,508, filed as application No. PCT/US2007/009448 on Apr. 17, 2007, now Pat. No. 8,247,629.

(60) Provisional application No. 60/808,192, filed on May 24, 2006.

(51) Int. Cl.
*C07C 2/66* (2006.01)
*C07C 6/12* (2006.01)

(52) U.S. Cl.
USPC ............................ 585/467; 585/323; 585/475

(58) Field of Classification Search
USPC .......................................... 585/467, 475, 323
See application file for complete search history.

(56) References Cited

U.S. PATENT DOCUMENTS

| | | | |
|---|---|---|---|
| 3,293,192 A | 12/1966 | Maher et al. | |
| 3,308,069 A | 3/1967 | Wadlinger et al. | |
| 3,442,795 A | 5/1969 | Kerr et al. | |
| 3,449,070 A | 6/1969 | McDaniel et al. | |
| 3,524,820 A | 8/1970 | Hemminger | |
| 3,674,680 A | 7/1972 | Hoekstra et al. | |
| 3,702,886 A | 11/1972 | Argauer et al. | |
| 3,709,979 A | 1/1973 | Chu | |
| 3,751,504 A | 8/1973 | Keown et al. | |
| 3,751,506 A | 8/1973 | Burress | |
| 3,755,483 A | 8/1973 | Burress | |
| 3,766,093 A | 10/1973 | Chu | |
| 3,832,449 A | 8/1974 | Rosinski et al. | |
| RE28,341 E | 2/1975 | Wadlinger et al. | |
| 3,894,104 A | 7/1975 | Chang et al. | |
| 3,923,636 A | 12/1975 | Mead et al. | |
| 3,966,644 A | 6/1976 | Gustafson | |
| 3,972,983 A | 8/1976 | Ciric | |
| 4,016,218 A | 4/1977 | Haag et al. | |
| 4,016,245 A | 4/1977 | Plank et al. | |
| 4,028,227 A | 6/1977 | Gustafson | |
| 4,076,842 A | 2/1978 | Plank et al. | |
| RE29,948 E | 3/1979 | Dwyer et al. | |
| 4,185,040 A * | 1/1980 | Ward et al. ...................... 502/64 |
| 4,234,231 A | 11/1980 | Yan | |
| 4,328,130 A | 5/1982 | Kyan | |
| 4,401,556 A | 8/1983 | Bezman et al. | |
| 4,439,409 A | 3/1984 | Puppe et al. | |
| 4,441,990 A | 4/1984 | Huang | |
| 4,556,477 A | 12/1985 | Dwyer | |
| 4,826,667 A | 5/1989 | Zones et al. | |
| 4,891,458 A | 1/1990 | Innes et al. | |
| 4,954,325 A | 9/1990 | Rubin et al. | |
| 4,992,606 A | 2/1991 | Kushnerick et al. | |
| 5,043,509 A | 8/1991 | Imai et al. | |
| 5,077,445 A | 12/1991 | Le | |
| 5,118,896 A | 6/1992 | Steigelmann et al. | |
| 5,149,894 A | 9/1992 | Holtermann et al. | |
| 5,236,575 A | 8/1993 | Bennett et al. | |
| 5,250,277 A | 10/1993 | Kresge et al. | |
| 5,258,565 A | 11/1993 | Kresge et al. | |
| 5,292,698 A | 3/1994 | Chu et al. | |
| 5,334,795 A | 8/1994 | Chu et al. | |
| 5,362,697 A | 11/1994 | Fung et al. | |

(Continued)

FOREIGN PATENT DOCUMENTS

| | | |
|---|---|---|
| CN | 1277893 | 12/2000 |
| CN | 1443603 | 9/2003 |

(Continued)

OTHER PUBLICATIONS

U.S. Appl. No. 60/808,192, filed May 24, 2006, Clark et al.

*Primary Examiner* — Thuan D Dang
(74) *Attorney, Agent, or Firm* — Darryl M. Tyus

(57) ABSTRACT

A process for producing a monoalkylated aromatic compound in an alkylation reaction zone, said process comprising the steps of:
(a) providing a first catalytic particulate material which comprises MCM-56 and having a ratio of surface area over volume ratio greater than about 79 $cm^{-1}$,
(b) providing said alkylation reaction zone with an alkylatable aromatic compound, an alkylating agent, and said first catalytic particulate material; and
(c) contacting said alkylatable aromatic compound and said alkylating agent with said catalytic particulate material in said alkylation reaction zone maintained under alkylation conditions, to form a product comprised of said monoalkylated aromatic compound and polyalkylated aromatic compound(s).

13 Claims, No Drawings

(56) References Cited

U.S. PATENT DOCUMENTS

| | | |
|---|---|---|
| 5,371,310 A | 12/1994 | Bennett et al. |
| 5,453,554 A | 9/1995 | Cheng et al. |
| 5,508,065 A | 4/1996 | Weiner |
| 5,557,024 A | 9/1996 | Cheng et al. |
| 5,789,640 A | 8/1998 | Jin et al. |
| 6,005,152 A | 12/1999 | Amarilli et al. |
| 6,077,498 A | 6/2000 | Diaz Cabañas et al. |
| 6,888,037 B2 * | 5/2005 | Dandekar et al. ............ 585/467 |
| 6,897,346 B1 | 5/2005 | Merrill et al. |
| 7,816,574 B2 | 10/2010 | Clark et al. |
| 7,928,274 B2 | 4/2011 | Clark et al. |
| 2002/0013216 A1 | 1/2002 | Broekhoven et al. |
| 2005/0113617 A1 | 5/2005 | Nanda |

FOREIGN PATENT DOCUMENTS

| | | |
|---|---|---|
| DE | 3315105 | 11/1983 |
| EP | 0 220 933 | 5/1987 |
| EP | 0 293 032 | 7/1993 |
| EP | 0 629 549 | 12/1994 |
| EP | 0 432 814 | 9/1995 |
| EP | 0 719 750 | 7/1996 |
| EP | 0 732 146 | 3/2006 |
| JP | 5-57193 | 9/1993 |
| JP | 11-60515 | 2/1999 |
| WO | WO 97/17290 | 5/1997 |
| WO | WO 01/21562 | 3/2001 |
| WO | WO 01/91901 | 12/2001 |
| WO | WO 2004/007072 | 1/2004 |
| WO | WO 2005/118476 | 12/2005 |
| WO | WO 2007/139629 | 12/2007 |

* cited by examiner

US 8,524,967 B2

MONOALKYLATED AROMATIC COMPOUND PRODUCTION

CROSS REFERENCE TO RELATED APPLICATIONS

This application is a continuation of U.S. application Ser. No. 13/537,811, filed Jun. 29, 2012, now U.S. Pat. No. 8,357, 830, which is a continuation of U.S. application Ser. No. 12/299,508, filed Jun. 18, 2009, now U.S. Pat. No. 8,247,629, which is a U.S. national stage application under 35 U.S.C. 371 of International Application PCT/US2007/009448 having an international filing date of Apr. 17, 2007, which claims the benefit of U.S. Provisional Application No. 60/808,192, filed May 24, 2006, the entireties of which are incorporated by reference.

FIELD

The present invention relates to a process for producing monoalkylated aromatic products, particularly ethylbenzene and cumene.

BACKGROUND

Ethylbenzene is a key raw material in the production of styrene and is produced by the reaction of ethylene and benzene in the presence of an acid alkylation catalyst. Older ethylbenzene production plants, those preferably built before 1980, used $AlCl_3$ or $BF_3$ as the acidic alkylation catalyst. Plants built after 1980 have in general used zeolite-based acidic catalysts as the alkylation catalyst.

Three types of ethylation reactor systems are used for producing ethylbenzene, namely, vapor phase reactor systems, liquid phase reactor systems, and mixed phase reactor systems.

In vapor-phase reactor systems, the ethylation reaction of benzene and ethylene is carried out at a temperature of about 350 to 450° C. and a pressure of 690-3534 KPa-a (6-35 $kg/cm^2$-g) in multiple fixed beds of zeolite catalyst. Ethylene exothermically reacts with benzene in the presence of such zeolite catalyst to form ethylbenzene, although undesirable reactions also occur. About 15 mol. % of the ethylbenzene formed further reacts with ethylene to form di-ethylbenzene isomers (DEB), tri-ethylbenzene isomers (TEB) and heavier aromatic products (heavies). All these undesirable reaction products, namely DEBs, TEBs and heavies, are often commonly referred to as polyethylated benzenes (PEBs).

By way of example, vapor phase ethylation of benzene over a catalyst comprising crystalline aluminosilicate zeolite ZSM-5 is disclosed in U.S. Pat. Nos. 3,751,504 (Keown et al.), 3,751,506 (Burress), and 3,755,483 (Burress).

In recent years the trend in industry has been to shift away from vapor phase ethylbenzene reactors in favor of liquid phase reactors. Liquid phase reactors operate at a temperature of about 150-280° C., which is below the critical temperature of benzene (290° C.). The rate of the ethylation reaction in a liquid phase reaction is lower as compared to a comparable vapor phase reaction. Hence, the catalyst volumes required for the liquid phase reaction are greater than those for the vapor phase reaction, but the lower design temperature of the liquid phase reaction economically compensates for the negatives associated with the higher catalyst volume.

Liquid phase ethylation of benzene using a catalyst comprising zeolite beta is disclosed in U.S. Pat. No. 4,891,458 and European Patent Publication Nos. 0432814 and 0629549. More recently it has been disclosed that MCM-22 and its structural analogues have utility in these alkylation/transalkylation reactions, for example, U.S. Pat. No. 4,992,606 (MCM-22), U.S. Pat. No. 5,258,565 (MCM-36), U.S. Pat. No. 5,371, 310 (MCM-49), U.S. Pat. No. 5,453,554 (MCM-56), U.S. Pat. No. 5,149,894 (SSZ-25); U.S. Pat. No. 6,077,498 (ITQ-1); International Patent Publication Nos. WO97/17290 and WO01/21562 (ITQ-2).

Typically, the zeolite catalysts employed in hydrocarbon conversion processes, such as aromatics alkylation, are in the form of cylindrical extrudates. However, it is known from, for example, U.S. Pat. No. 3,966,644 that shaped catalyst particles having a high surface to volume ratio, such as those having a polylobal cross-section, can produce improved results in processes which are diffusion limited, such as the hydrogenation of reside.

Moreover, it is known from U.S. Pat. No. 4,441,990 that a polylobal catalyst particle having a non-cylindrical centrally located aperture can reduce the diffusion path for reagents and the pressure drop across packed catalyst beds while minimizing catalyst loss due to breakage, abrasion and crushing. In particular, Example 8 of the '990 patent discloses that hollow trilobal and quadrilobal ZSM-5 catalysts are more active and selective for the ethylation of benzene at 770° F. and 300 psig pressure than solid cylindrical catalysts of the same length. Under these conditions, the reagents are necessarily in the vapor phase.

U.S. Pat. No. 6,888,037 disclosed a process for producing cumene which comprises the step of contacting benzene and propylene under at least partial liquid phase alkylating conditions with a particulate molecular sieve alkylation catalyst, wherein the particles of said alkylation catalyst have a surface to volume ratio of about 80 to less than 200 $inch^{-1}$. According to U.S. Pat. No. 6,888,037, the liquid phase propylation of benzene, unlike the liquid phase ethylation of benzene, is sensitive to intraparticle (macroporous) diffusion limitations. In particular, by selecting the shape and size of the particles of the alkylation catalyst such that the surface to volume ratio is within the specified range, the intraparticle diffusion distance can be decreased without excessively increasing the pressure drop across the first catalyst bed. As a result, the activity of the catalyst for the propylation of benzene can be increased, while at the same time the selectivity of the catalyst towards undesirable polyalkylated species, such as diisopropylbenzene (DIPB) can be reduced.

Surprisingly, however, it has now been found that size and shape of the catalyst particles beyond the range disclosed in the U.S. Pat. No. 6,888,037 can yield improved results, e.g., activity and/or selectivity in the liquid phase alkylation of benzene to produce monoalkylbenzene, such as ethylbenzene and cumene.

SUMMARY OF THE DISCLOSURE

In some embodiments, this disclosure relates to a process for producing a monoalkylated aromatic compound in an alkylation reaction zone, said process comprising the steps of:
(a) providing a first catalytic particulate material having a ratio of surface area over volume ratio greater than about 79 $cm^1$;
(b) providing said alkylation reaction zone with an alkylatable aromatic compound, an alkylating agent, and said first catalytic particulate material; and
(c) contacting said alkylatable aromatic compound and said alkylating agent with said catalytic particulate material in said alkylation reaction zone maintained under alkylation conditions, to form a product comprised of said monoalkylated aromatic compound and polyalkylated aromatic compound(s);

whereby the molar ratio of said polyalkylated aromatic compound(s) over said monoalkylated aromatic compound produced by said first catalytic particulate material is less than the molar ratio of polyalkylated aromatic compound(s) over monoalkylated aromatic compound produced by a second catalytic particulate material and said alkylation reaction zone is operated under the same alkylation conditions, wherein at least 51 wt. % of said second catalytic particulate material having a ratio of surface area over volume between 78 and 79 cm$^{-1}$.

In additional aspects of this disclosure, the moles of said monoalkylated aromatic compound in said product is increased as compared to the moles of said monoalkylated aromatic compound produced by said catalytic particulate material when majority of said catalytic particulate material has a surface area over volume ratio between 78 and 79 cm$^{-1}$ and said alkylation reaction zone is operated under the same alkylation conditions for the same amount of time with the same amount of catalytic particulate material mass.

In some embodiments of this disclosure, the monoalkylated aromatic compound comprises ethylbenzene, said alkylatable aromatic compound comprises benzene and said alkylating agent comprises ethylene. In additional embodiments of this disclosure, the said monoalkylated aromatic compound comprises cumene, said alkylatable aromatic compound comprises benzene and said alkylating agent comprises propylene. In further additional embodiments of this disclosure, said monoalkylated aromatic compound comprises sec-butyl-benzene, said alkylatable aromatic compound comprises benzene and said alkylating agent comprises butene.

Additionally, this disclosure relates to a process for producing ethylbenzene in an alkylation reaction zone, said process comprising the steps of:
(a) providing said alkylation reaction zone with an alkylatable aromatic compound comprising benzene, an alkylating agent comprising ethylene, and a catalytic particulate material; and
(b) contacting said alkylatable aromatic compound and said alkylating agent with said catalytic particulate material in said alkylation reaction zone maintained under alkylation conditions, to form a product comprised of said ethylbenzene and polyethylbenzene(s), wherein majority of said catalytic particulate material has a surface area over volume ratio of greater than about 79 cm$^{-1}$, and wherein the molar ratio of said polyethylbenzene(s) over said ethylbenzene in said product is reduced as compared to the molar ratio of said polyethylbenzene over said ethylbenzene produced by said catalytic particulate material when majority of said catalytic particulate material has a surface area over volume ratio between 78 and 79 cm$^{-1}$ and said alkylation reaction zone is operated under the same alkylation conditions.

In some additional embodiments, this disclosure relates to a process for producing cumene in an alkylation reaction zone, said process comprising the steps of:
(a) providing said alkylation reaction zone with an alkylatable aromatic compound comprising benzene, an alkylating agent comprising propylene, and a catalytic particulate material; and
(b) contacting said alkylatable aromatic compound and said alkylating agent with said catalytic particulate material in said alkylation reaction zone maintained under alkylation conditions, to form a product comprised of said cumene and polyisopropylbenzene(s), wherein majority of said catalytic particulate material has a surface area over volume ratio of greater than about 79 cm$^{-1}$, and wherein the molar ratio of said polyisopropylbenzene(s) over said cumene in said product is reduced as compared to the molar ratio of said polyisopropylbenzene(s) over said cumene produced by said catalytic particulate material when majority of said catalytic particulate material has a surface area over volume ratio between 78 and 79 cm$^{-1}$ and said alkylation reaction zone is operated under the same alkylation conditions.

In some further embodiments, this disclosure relates to a process for producing a monoalkylated aromatic compound, which is suitable for retrofitting an existing ethylbenzene or cumene plant with a vapor, liquid, or mixed phase alkylation reactor having at least one alkylation reaction zone, comprising the steps of:
(a) providing said alkylation reaction zone with an alkylatable aromatic compound, an alkylating agent, and a catalytic particulate material; and
(b) contacting said alkylatable aromatic compound and said alkylating agent with said catalytic particulate material in said alkylation reaction zone maintained under alkylation conditions, to form a product comprised of said monoalkylated aromatic compound and polyalkylated aromatic compound(s), wherein majority of said catalytic particulate material has a surface area over volume ratio of greater than about 79 cm$^{-1}$.

In some aspects of this disclosure majority of said catalytic particulate material has a surface area over volume ratio of greater than about 236 cm$^{-1}$, preferably greater than about 1575 cm$^{-1}$ or 3150 cm$^{-1}$.

The catalytic particulate material is made by a process selected from the group consisting of spray drying, crushing, chopping, extrusion, sieving, size reduction of formed catalyst, or any combination thereof.

In some embodiments, said catalytic particulate material comprises a molecular sieve having a channel size greater than 5 Å. The molecular sieve has a framework structure selected from the group consisting of *BEA, MWW, and FAU.

In a preferred embodiment, said molecular sieve is a MCM-22 family material. In a more preferred embodiment, the MCM-22 family material is selected from the group consisting of ERB-1, ITQ-1, PSH-3, SSZ-25, MCM-22, MCM-36, MCM-49, MCM-56, and combinations thereof.

In some aspects of this disclosure, the alkylation conditions include a temperature from about 20° C. to about 400° C., a pressure from about 20.3 to 4800 kPa-a, a weight hourly space velocity (WHSV) from about 0.1 to about 500 h$^{-1}$ based on the weight of the alkylating agent, and a molar ratio of said alkylatable compound over said alkylating agent from about 0.1:1 to 50:1.

The product comprises polyalkylated aromatic compound(s), preferably the process of this disclosure further comprises steps of:
(c) separating said polyalkylated aromatic compound(s) from said product to form a transalkylation feed stream; and
(d) contacting at least a portion of said transalkylation feed stream with a feedstock comprising an alkylatable aromatic compound in the presence of a transalkylation catalyst to produce a transalkylation effluent in a transalkylation reaction zone maintained under transalkylation conditions, said transalkylation effluent which comprises said monoalkylated aromatic compound.

Preferably the transalkylation catalyst comprises a molecular sieve selected from the group consisting of MCM-22, MCM-36, MCM-49 and MCM-56, beta zeolite, faujasite, mordenite, TEA-mordenite, PSH-3, SSZ-25, ERB-1, ITQ-1, ITQ-2, zeolite Y, Ultrastable Y (USY), Dealuminized Y, rare earth exchanged Y (REY), ZSM-3, ZSM-4, ZSM-18, ZSM-20, or any combination thereof.

Preferably said transalkylation conditions include a temperature of 100 to 300° C. and a pressure of 696 to 4137 kPa-a, a WHSV based on the weight of said polyalkylated aromatic compound(s) of about 0.5 to 200 $h^{-1}$, a molar ratio of said alkylatable aromatic compound to said polyalkylated aromatic compound(s) of 05:1 to 30:1.

These and other facets of the present invention shall become apparent from the following detailed description, figure, and appended claims.

DETAILED DESCRIPTION OF THE PREFERRED EMBODIMENTS

Feedstocks

The reactants used in the process of the disclosure include an alkylatable aromatic compound and an alkylating agent. As used herein, an "alkylatable aromatic compound" is a compound that may receive an alkyl group and an "alkylating agent" is a compound which may donate an alkyl group to an alkylatable aromatic compound.

The term "aromatic" as used herein is to be understood in accordance with its art-recognized scope which includes substituted and unsubstituted mono- and polynuclear compounds. Compounds of an aromatic character, which possess a heteroatom, are also useful.

Substituted aromatic compounds which may be used for the disclosure should possess at least one hydrogen atom directly bonded to the aromatic nucleus. The aromatic rings may be substituted with one or more alkyl, aryl, alkaryl, alkoxy, aryloxy, cycloalkyl, halide, and/or other groups which do not interfere with the alkylation reaction.

Suitable aromatic compounds that may be used for this disclosure include benzene, naphthalene, anthracene, naphthacene, perylene, coronene, and phenanthrene, with benzene being preferred.

Suitable alkyl substituted aromatic compounds that may be used for this disclosure include toluene, xylene, isopropylbenzene, normal propylbenzene, alpha-methylnaphthalene, ethylbenzene, mesitylene, durene, cymenes, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic hydrocarbons may also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecytoluene, etc. Very often alkylate is obtained as a high boiling fraction in which the alkyl group attached to the aromatic nucleus varies in size from about $C_6$ to about $C_{12}$.

Reformate streams that may contain substantial quantities of benzene, toluene and/or xylene may be particularly suitable feed for the process of this disclosure. Although the process is particularly directed to the production of ethylbenzene or cumene, it is equally applicable to the production of other $C_7$-$C_{20}$ alkylaromatic compounds, such as $C_8$-$C_{16}$ linear and near linear alkylbenzenes.

Suitable alkylating agent(s) that may be used in this disclosure comprise alkene compound(s) and/or alcohol compound(s), and mixtures thereof. Other suitable alkylating agents that may be useful in the process of this disclosure generally include any aliphatic or aromatic organic compound having one or more available alkylating aliphatic groups capable of reaction with the alkylatable aromatic compound. Examples of suitable alkylating agents are $C_2$-$C_{16}$ olefins such as $C_2$-$C_5$ olefins, viz., ethylene, propylene, the butenes, and the pentenes; $C_1$-$C_{12}$ alkanols (inclusive of monoalcohols, dialcohols, trialcohols, etc.), preferably $C_1$-$C_5$ alkanols, such as methanol, ethanol, the propanols, the butanols, and the pentanols; $C_2$-$C_{20}$ ethers, e.g., $C_2$-$C_5$ ethers including dimethylether and diethylether; aldehydes such as formaldehyde, acetaldehyde, propionaldehyde, butyraldehyde, and n-valeraldehyde; and alkyl halides such as methyl chloride, ethyl chloride, the propyl chlorides, the butyl chlorides, and the pentyl chlorides, and so forth. It is generally preferred that the alkylating agent has no greater than 5 carbon atoms, more preferably no greater than 3 carbon atoms. Thus the alkylating agent may preferably be selected from the group consisting of $C_2$-$C_5$ olefins and $C_1$-$C_5$ alkanols. The alkylating agent includes a concentrated alkene feedstock (e.g., polymer grade olefins) and a dilute alkene feedstock (e.g., catalytic cracking off-gas).

Alkylation and Transalkylation Reactions

The alkylation reaction zone is operated under alkylation conditions. The alkylation conditions of the reaction zone comprise temperature, pressure, the composition of the alkylatable aromatic compound(s) to the composition of the alkylating agent, and the alkylatable aromatic compound(s) to alkylating agent ratio (molar ratio).

In addition to, and upstream of, the alkylation zones, the alkylation reaction system may also include a by-passable reactive guard bed typically located in a pre-reactor separate from the remainder of the alkylation reactor. The reactive guard bed may also loaded with alkylation catalyst, which may be same or different from the catalyst used in the multi-stage alkylation reaction system. The reactive guard bed is maintained from under ambient or up to alkylation conditions. At least a portion of alkylatable aromatic compound and preferably at least a portion of the second feedstock are passed through the reactive guard bed prior to entry into the first reaction zone of the alkylation reaction zones in the reactor. The reactive guard bed not only serves to affect the desired alkylation reaction but is also used to remove any reactive impurities in the feeds, such as nitrogen compounds, which could otherwise poison the remainder of the alkylation catalyst. The catalyst in the reactive guard bed is therefore subject to more frequent regeneration and/or replacement than the remainder of the alkylation catalyst and hence the guard bed is normally provided with a by-pass circuit so that the alkylation feedstock can be fed directly to the series connected alkylation reaction zones in the reactor when the guard bed is out of service. The reactive guard bed operates in predominantly liquid phase and in co-current upflow or downflow operation.

The alkylation reactor used in the process of the present invention is normally operated so as to achieve essentially complete conversion of the alkene. However, for some applications, it may be desirable to operate at below 100% alkene conversion. The employment a separate finishing reactor downstream of the multi-zones alkylation reactor may be desirable under certain conditions. The finishing reactor would also contain alkylation catalyst, which could be same or different from the catalyst used in the alkylation reactor and could be maintained under predominantly liquid phase alkylation conditions.

The alkylation reactor used in the process of the present invention is highly selective to the desired monoalkylated product, such as ethylbenzene, but normally produces at least some polyalkylated species, such as dialkylated aromatic compound(s). Optionally the effluent from the alkylation reaction zone may be supplied to a transalkylation reaction zone which is normally separate from the alkylation reaction zone. The transalkylation reaction zone produces additional monoalkylated product by reacting the polyalkylated species with alkylatable aromatic compound.

The alkylation reaction zone is maintained under suitable alkylation conditions. The alkylation conditions comprise temperature, pressure, alkylatable aromatic compound(s) to alkylating agent ratio, and alkene to alkane ratio. In one embodiment, the alkylation conditions include a temperature of 20 to 400° C. and a pressure of 20.3 to 4800 kPa-a, preferably, a pressure of 20.3 to 4601 kPa-a, optionally, from about 20.3 to about 2500 kPa-a, a WHSV based on the weight of the alkylating agent for overall reactor of 0.1 to 500 $h^{-1}$, preferably, 0.1 to 10 $h^{-1}$, more preferably, 0.5 to 5 $h^{-1}$, and a molar ratio of alkylatable aromatic compound to alkylating agent from about 0.1:1 to about 50:1, preferably from about 0.1:1 to about 10:1. In some embodiments, the alkylation reaction zone is maintained in predominately liquid phase. The alkylation conditions for predominately liquid phase alkylation include a temperature of 100 to 260° C. and a pressure of 689 to 4601 kPa-a, preferably, a pressure of 1500 to 3500 kPa-a, a WHSV based on alkylating agent for overall reactor of 0.1 to 50 $h^{-1}$, preferably, 0.1 to 10 $h^{-1}$, more preferably, 0.5 to 5 $h^{-1}$, and a molar ratio of alkylatable aromatic compound to alkylating agent from about 0.1:1 to about 50:1, preferably from about 0.1:1 to about 10:1.

The term "predominately liquid phase" used herein is understood as having at least 95 wt. % liquid phase, preferably, 98 wt. %, more preferably, 99 wt. %, and most preferably, 99.5 wt. %.

Particular conditions for carrying out the liquid phase alkylation of benzene with ethylene may include a temperature of from about 100 to 300° C., preferably, a temperature of from about 150 to 260° C., a pressure of 689 to 4601 kPa-a (100 to 667 psia), preferably, a pressure of 1500 to 3000 kPa-a (218 to 435 psia), a WHSV based on ethylene for overall reactor of 0.1 to 200 $h^{-1}$, preferably, 0.2 to 20 $h^{-1}$, more preferably, 0.5 to 10 $h^{-1}$, or a WHSV based on both ethylene and benzene for overall reactor of 10 to 100 $h^{-1}$, preferably, 20 to 50 $h^{-1}$, and a molar ratio of benzene to ethylene from about 0.1 to about 10, preferably from about 1:1 to 10:1.

Particular conditions for carrying out the predominantly liquid phase alkylation of benzene with propylene may include a temperature of from about 20 to 200° C., a pressure of about 680 to about 4800 kPa-a; preferably from about 100 to 140° C. and pressure of about 2000 to 3000 kPa-a, a WHSV based on propylene of from about 0.1 about 200 $hr^{-1}$, and a molar ratio of benzene to ethylene from about 01:1 to about 50:1, preferably from about 1:1 to 10:1.

Where the alkylation system includes a reactive guard bed, it is maintained under at least partial liquid phase conditions. The guard bed will preferably operate at a temperature of from about 120 to 285° C., preferably, a temperature of from about 150 to 260° C., a pressure of 689 to 4601 kPa-a (100 to 667 psia), preferably, a pressure of 1500 to 3000 kPa-a (218 to 435 psia), a WHSV based on alkylating agent for overall reactor of 0.1 to 10 $h^{-1}$, preferably, 0.2 to 2 $h^{-1}$, more preferably, 0.5 to 1 $h^{-1}$, or a WHSV based on both alkylating agent and alkylatable aromatic compound for overall reactor of 10 to 100 $h^{-1}$, preferably, 20 to 50 $h^{-1}$, and a molar ratio of alkylatable aromatic compound to alkylating agent from about 1 to about 10.

The polyalkylated aromatic compound(s) in the effluents may be separated for transalkylation with alkylatable aromatic compound(s). The alkylated aromatic compound is made by transalkylation between polyalkylated aromatic compound(s) and the alkylatable aromatic compound.

The transalkylation reaction takes place under predominantly liquid phase conditions. Particular conditions for carrying out the predominantly liquid phase transalkylation of polyalkylated aromatic compound(s) with alkylatable aromatic compound may include a temperature of from about 100° to about 300° C., a pressure of 696 to 4137 kPa-a, a WHSV based on the weight of the polyalkylated aromatic compound(s) feed to the reaction zone of from about 0.5 to about 200 $hr^{-1}$ and a molar ratio of alkylatable aromatic compound to polyalkylated aromatic compound(s) of from 0.5:1 to 30:1, preferably, 1:1 to 10:1, more preferably, 1:1 to 5:1.

In additional embodiments, the transalkylation reaction takes place under vapor phase conditions. Particular conditions for carrying out the vapor phase transalkylation of polyethylbenzenes with benzene may include a temperature of from about 350 to about 450° C., a pressure of 696 to 1601 kPa-a, a WHSV based on the weight of the polyethylbenzene (s) feed to the reaction zone of from about 0.5 to about 20 $hr^{-1}$, preferably, from about 1 to about 10 $hr^{-1}$, and a molar ratio of benzene to polyethylbenzene(s) of from 1:1 to 5:1, preferably, 2:1 to 3:1.

In some embodiments, the monoalkylated aromatic compound comprises ethylbenzene, the alkylatable aromatic compound comprises benzene and the alkylating agent comprises ethylene.

In additional embodiments, the monoalkylated aromatic compound comprises cumene, the alkylatable aromatic compound comprises benzene and the alkylating agent comprises propylene.

In further additional embodiments, the monoalkylated aromatic compound comprises sec-butyl-benzene, the alkylatable aromatic compound comprises benzene and the alkylating agent comprise butene.

In some alternative embodiments of this disclosure, the above mentioned processes are suitable for retrofitting an existing ethylbenzene or cumene plant with a vapor, liquid, or mixed phase alkylation reactor. In particular, the process of this disclosure may be used to retrofit an existing ethylbenzene or cumene plant using polymer grade or chemical grade ethylene or propylene with minimum amount of new equipment, such as, extra compressors for the second feedstock, extra-separation column for light gas and aromatics, and other equipment.

As used herein, the term "retrofit" means to install new or modified process reactors, conduits, pumps and other equipment to a previously constructed processing plant.

Catalysts

The alkylation and transalkylation catalyst used in the process of the disclosure is not critical but normally comprising at least one of MCM-22 family material (e.g., MCM-22, MCM-49, MCM-36, MCM-56, PSH-3, SSZ-25, ERB-1, ITQ-1, ITQ-2) beta zeolite, faujasite, mordenite, TEA-mordenite, and optionally SAPO molecular sieves (e.g., SAPO-34 and SAPO-41).

The term "MCM-22 family material" (or "material of the MCM-22 family" or "molecular sieve of the MCM-22 family"), as used herein, includes:

a. molecular sieves made from a common first degree crystalline building block "unit cell having the MWW framework topology". A unit cell is a spatial arrangement of atoms which is tiled in three-dimensional space to describe the crystal as described in the "Atlas of Zeolite Framework Types", Fifth edition, 2001, the entire content of which is incorporated as reference;

b. molecular sieves made from a common second degree building block, a 2-dimensional tiling of such MWW framework type unit cells, forming a "monolayer of one unit cell thickness", preferably one c-unit cell thickness;

c. molecular sieves made from common second degree building blocks, "layers of one or more than one unit cell thickness", wherein the layer of more than one unit cell thickness is made from stacking, packing, or binding at least two monolayers of one unit cell thick. The stacking of such second degree building blocks can be in a regular fashion, an irregular fashion, a random fashion, or any combination thereof; or d. molecular sieves made by any regular or random 2-dimensional or 3-dimensional combination of unit cells having the MWW framework topology.

The MCM-22 family materials are characterized by having an X-ray diffraction pattern including d-spacing maxima at 12.4±0.25, 3.57±0.07 and 3.42±0.07 Angstroms (either calcined or as-synthesized). The MCM-22 family materials may also be characterized by having an X-ray diffraction pattern including d-spacing maxima at 12.4±0.25, 6.9±0.15, 3.57±0.07 and 3.42±0.07 Angstroms (either calcined or as-synthesized). The X-ray diffraction data used to characterize said molecular sieve are obtained by standard techniques using the K-alpha doublet of copper as the incident radiation and a diffractometer equipped with a scintillation counter and associated computer as the collection system. Materials belong to the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), ITQ-30 (described in International Patent Publication No. WO2005118476), MCM-36 (described in U.S. Pat. No. 5,250,277), MCM-49 (described in U.S. Pat. No. 5,236,575) and MCM-56 (described in U.S. Pat. No. 5,362,697). The entire contents of said patents are incorporated herein by reference.

It is to be appreciated the MCM-22 family molecular sieves described above are distinguished from conventional large pore zeolite alkylation catalysts, such as mordenite, TEA-mordenite, in that the MCM-22 materials have 12-ring surface pockets which do not communicate with the 10-ring internal pore system of the molecular sieve.

The zeolitic materials designated by the IZA-SC as being of the MWW topology are multi-layered materials which have two pore systems arising from the presence of both 10 and 12 membered rings. The Atlas of Zeolite Framework Types classes five differently named materials as having this same topology: MCM-22, ERB-1, ITQ-1, PSH-3, and SSZ-25.

MCM-22 and its use to catalyze the synthesis of alkylaromatics, including ethylbenzene, is described in U.S. Pat. Nos. 4,992,606; 5,077,445; and 5,334,795. PSH-3 is described in U.S. Pat. No. 4,439,409. SSZ-25 and its use in aromatics alkylation are described in U.S. Pat. No. 5,149,894. ERB-1 is described in European Patent No. 0293032. ITQ-1 is described in U.S. Pat. No. 6,077,498. ITQ-2 is described in International Patent Publication No. WO97/17290 and WO01/21562. MCM-36 is described in U.S. Pat. Nos. 5,250,277 and 5,292,698. U.S. Pat. No. 5,258,565 describes the synthesis of alkylaromatics, including ethylbenzene, using a catalyst comprising MCM-36. MCM-49 is described in U.S. Pat. No. 5,236,575. The use of MCM-49 to catalyze the synthesis of alkylaromatics, including ethylbenzene, is described in U.S. Pat. Nos. 5,508,065 and 5,371,310. MCM-56 is described in U.S. Pat. No. 5,362,697. The use of MCM-56 to catalyze the synthesis of alkylaromatics including ethylbenzene is described in U.S. Pat. Nos. 5,557,024 and 5,453,554. The entire contents of all the above patent specifications are incorporated herein by reference.

Alternatively, the alkylation and transalkylation catalyst can comprise a medium pore molecular sieve having a Constraint Index of 2-12 (as defined in U.S. Pat. No. 4,016,218), including ZSM-5, ZSM-11, ZSM-12, ZSM-22, ZSM-23, ZSM-35, and ZSM-48. ZSM-5 is described in detail in U.S. Pat. Nos. 3,702,886 and Re. 29,948. ZSM-11 is described in detail in U.S. Pat. No. 3,709,979. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234,231. The entire contents of all the above patent specifications are incorporated herein by reference. In some embodiments, the alkylation and transalkylation catalyst can comprise a medium pore molecular sieve having a channel size greater than 5 Å.

As a further alternative, the alkylation and transalkylation catalyst can comprise a large pore molecular sieve having a Constraint Index less than 2. Suitable large pore molecular sieves include zeolite beta, zeolite Y, Ultrastable Y (USY), Dealuminized Y (DealY), mordenite, TEA-mordenite, ZSM-3, ZSM-4, ZSM-18, and ZSM-20. Zeolite ZSM-14 is described in U.S. Pat. No. 3,923,636. Zeolite ZSM-20 is described in U.S. Pat. No. 3,972,983. Zeolite Beta is described in U.S. Pat. Nos. 3,308,069, and Re. No. 28,341. Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Zeolite UHP-Y is described in U.S. Pat. No. 4,401,556. Rare earth exchanged Y (REY) is described in U.S. Pat. No. 3,524,820. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104. The entire contents of all the above patent specifications are incorporated herein by reference.

In some embodiments, the molecular sieves may be used for the alkylation reaction in this disclosure include a molecular sieve having a channel size greater than 5 Å, such as a MCM-22 family material. Examples of the MCM-22 family material useful in this disclosure are ERB-1, ITQ-1, PSH-3, SSZ-25, MCM-22, MCM-36, MCM-49, MCM-56, and combinations thereof. Other molecular sieves may be useful as alkylation catalyst in disclosure are molecular sieves having a framework structure selected from the group consisting of *BEA, MWW, and FAU.

Same catalyst may be used in both the transalkylation zone and the alkylation zones of the present invention. Preferably, however, catalysts are chosen for the different alkylation zones and the transalkylation zone, so as to be tailored for the particular reactions catalyzed therein. In some embodiments of the present invention, a standard activity catalyst for example, 50% zeolite and 50% binder is used in the higher temperature alkylation catalyst beds and a higher activity catalyst for example, 75% zeolite and 25% binder is used in the lower temperature alkylation catalyst beds, while suitable transalkylation catalyst is used in the transalkylation zone. In such an embodiment, any finishing reactor zone could include a MCM-22 catalyst bed for predominantly liquid phase operation.

According to the disclosure, it has now been found that the liquid phase alkylation of benzene is sensitive to the shape and size of the particles of the alkylation catalyst. When the majority of the catalyst particles has a surface to volume ratio of higher than 79 $cm^{-1}$, the activity and the mono-selectivity for producing monoalkylbenzene improves when the surface to volume ratio of the majority of the catalyst particles increases. Both activity and mono-selectivity of an alkylation catalyst improves when the surface to volume ratio of the majority of the catalyst particles is higher than 79 $cm^{-1}$, preferably higher than 236, more preferably higher than 1575, and most preferably higher than 3150 $cm^{-1}$.

The term "the majority of the catalyst particles" as used herein means at least 51 wt. %, preferable at least 80 wt %, most preferably majority of the catalyst particles.

The activity of an alkylation catalyst is defined as the amount of monoalkylated aromatic compound (e.g., monoalkylbenzene) produced per unit amount of time per unit amount of catalyst used at certain conditions. The activity of an alkylation catalyst was measured in this disclosure using the kinetic rate constant of a second order reaction kinetics. The relative activity of two alkylation catalysts can be compared by comparing their activities under exact the same alkylation conditions. The alkylation conditions comprise temperature, pressure, composition of feedstock (alkylatable aromatic compound and alkylating agent), and weight-hourly-space-velocity (WHSV).

One by-product of alkylation reaction is polyalkylated aromatic compound(s) (e.g., bialkylbenzene(s)). The selectivity to monoalkylated aromatic compound of an alkylation catalyst is defined as the moles of monoalkylated aromatic compound produced per mole of polyalkylated aromatic compound(s) produced. The relative selectivity of two alkylation catalysts can be compared by comparing their selectivities under exact the same alkylation conditions. The alkylation conditions comprise temperature, pressure, composition of feedstock (alkylatable aromatic compound and alkylating agent), and weight-hourly-space-velocity (WHSV).

Producing the alkylation catalyst with the desired surface to volume ratio can readily be achieved by controlling the particle size of the catalyst or by using a shaped catalyst particle, such as the grooved cylindrical extrudate described in U.S. Pat. No. 4,328,130 or a hollow or solid polylobal extrudate as described in U.S. Pat. No. 4,441,990, the entire contents of both of which are incorporated herein by reference. Other method of producing the alkylation catalyst with the desired surface to volume ratio may be used in this disclosure. Examples of methods of producing the alkylation catalyst with the desired surface to volume ratio are spray drying, crushing, chopping, extrusion, and sieving.

A summary of the molecular sieves and/or zeolites, in terms of production, modification and characterization of molecular sieves, is described in the book "Molecular Sieves—Principles of Synthesis and Identification"; (R. Szostak, Blackie Academic & Professional, London, 1998, Second Edition). In addition to molecular sieves, amorphous materials, chiefly silica, aluminum silicate and aluminum oxide, have been used as adsorbents and catalyst supports. A number of long-known techniques, like spray drying, prilling, pelletizing and extrusion, have been and are being used to produce macrostructures in the form of, for example, spherical particles, extrudates, pellets and tablets of both micropores and other types of porous materials for use in catalysis, adsorption and ion exchange. A summary of these techniques is described in "Catalyst Manufacture," A. B. Stiles and T. A. Koch, Marcel Dekker, New York, 1995.

Although the alkylation process of the disclosure is particularly selective towards the production of the desired monoalkylated species, the alkylation step will normally produce some polyalkylated species. Thus the process preferably includes the further steps of separating the polyalkylated species from the alkylation effluent and reacting them with additional alkylatable aromatic compound, e.g., benzene, in a transalkylation reactor over a suitable transalkylation catalyst. Preferably, the transalkylation reaction is conducted in a separate reactor from the alkylation reaction.

The disclosure will be more particularly described with reference to the following Examples.

The following Examples will serve to further illustrate the process and some advantages of the present invention. In the Examples, catalyst activity is defined by reference to the kinetic rate constant which is determined by assuming second order reaction kinetics. For a discussion of the determination of the kinetic rate constant, reference is directed to "Heterogeneous Reactions: Analysis, Examples, and Reactor Design, Vol. 2: Fluid-Fluid-Solid Reactions" by L. K. Doraiswamy and M. M. Sharma, John Wiley & Sons, New York (1994) and to "Chemical Reaction Engineering" by O. Levenspiel, Wiley Eastern Limited, New Delhi (1972).

In the Examples, catalyst selectivity is defined as the weight ratio of monoalkylbenzene over polyalkylbenzene in the product.

EXAMPLES

Feed Pretreatment
Benzene

Benzene was obtained from the ExxonMobil Baytown Chemical plant. The benzene was passed through a pretreatment vessel (2 L vessel) containing equal parts (by volume):
  a. 13X, 4A, Engelhard F-24 Clay, Selexsorb CD (in order from inlet to outlet); and then
  b. through a 250 ml vessel containing MCM-22 catalyst.
All feed pretreatment materials are dried in a 260° C. oven for 12 hours before using.
Propylene Propylene was obtained from Scott Specialty Gases and was polymer grade. Propylene was passed through a 300 ml vessel containing pretreatment materials in the following order:
  a. 150 ml molecular sieve 5A; and
  b. 150 ml Selexsorb CD.
Both pretreatment materials were dried in a 260° C. oven for 12 hours before using.
Ethylene Ethylene was obtained from Scott Specialty Gases and was polymer grade. Ethylene was passed through a 300 ml vessel containing pretreatment materials in the following order:
  a. 150 ml molecular sieve 5A; and
  b. 150 ml Selexsorb CD.
Both pretreatment materials were dried in a 260° C. oven for 12 hours before using.

Nitrogen

Nitrogen was ultra high purity grade and obtained from Scott Specialty Gases. Nitrogen was passed through a 300 ml vessel containing pretreatment materials in the following order;

a. 150 cc molecular sieve 5A; and
b. 150 ml Selexsorb CD.

Both pretreatment materials were dried in a 260° C. oven for 12 hours before using.

Cumene Batch Test Procedures

Equipment

A 300 ml Parr batch reaction vessel equipped with a stir rod and static catalyst basket was used for the activity and selectivity measurements. The reaction vessel was fitted with two removable vessels for the introduction of benzene and propylene respectively.

Catalyst Pretreatment and Loading

Two grams of catalyst were dried in oven (in air) at 260° C. for 2 hours. The catalyst was removed from the oven and immediately. A first layer of quartz chips was used to line the bottom of the basket followed by loading of one gram of the catalyst into the basket on top of the first layer of quartz chips. A second layer of quartz chips was then placed on top of the catalyst. The catalyst basket containing the catalyst and quartz chips was placed in an oven at 260° C. overnight in air (~16 hrs).

The reactor and all lines were cleaned with a suitable solvent (such as toluene) before each experiment. The reactor and all lines were dried in air after cleaning to remove all traces of cleaning solvent. The catalyst Basket containing the catalyst and quartz chips was removed from the oven and immediately placed in reactor and the reactor was immediately assembled.

Test Sequence

The reactor temperature was set to 170° C. and purged with 100 standard cubic milliliter of ultra high purity $N_2$ for 2 hours. After nitrogen had purged the reactor for two hours, reactor temperature was reduced to 130° C., the nitrogen purge was discontinued and the reactor vent closed. 156.1 g of benzene was loaded into a 300 ml transfer vessel, performed in a closed system. The benzene vessel was pressurized to 11622 kPa-a (100 psig) with ultra high purity nitrogen and the benzene was transferred into the reactor. The agitator speed was set to 500 rotation per minute (rpm) and the reactor was allowed to equilibrate for 1 hour. A 75 ml transfer vessel was then filled with 28.1 g liquid propylene and connected to the reactor vessel, and then connected with 31887 kPa-a (300 psig) ultra high purity nitrogen. After the one-hour benzene stir time had elapsed, the propylene was transferred from the vessel to the reactor. The 31887 kPa-a (300 psig) nitrogen source was maintained connected to propylene vessel and open to the reactor during the entire experiment to maintain constant reaction pressure during the test. Liquid samples were taken at 30, 60, 120, 150, 180 and 240 min after addition of the propylene.

Ethylbenzene Batch Test Procedure

Equipment

A 600 ml Parr batch reaction vessel equipped with a stir rod and static catalyst basket was used for the activity and selectivity measurements. The reaction vessel was fitted with a removable vessel for the introduction of benzene.

Catalyst Pretreatment and Loading

Two grams of catalyst were dried in oven (in air) at 260° C. for 2 hours. The catalyst was removed from the oven and immediately loaded into the catalyst basket. A first layer of quartz chips was used to line the bottom of the basket followed by loading of five grams of the catalyst into the basket on top of the first layer of quartz chips. A second layer of quartz chips was then placed on top of the catalyst. The catalyst basket containing the catalyst and quartz chips was placed in an oven at 260° C. overnight in air (~16 hrs).

The reactor and all lines were cleaned with a suitable solvent (such as toluene) before each experiment. The reactor and all lines were dried in air after cleaning to remove all traces of cleaning solvent. The catalyst basket containing the catalyst and quartz chips was removed from the oven and immediately placed in reactor and the reactor was immediately assembled.

Test Sequence

The reactor temperature was set to 170° C. and purged with 100 standard cubic milliliter of ultra high purity $N_2$ for 2 hours. After nitrogen had purged the reactor for two hours, reactor temperature was increased to 220° C., the nitrogen purge was discontinued and the reactor vent closed. 195 grams of benzene was loaded into a 600 ml transfer vessel, performed in a closed system. The benzene vessel was pressurized to 11622 kPa-a (100 psig) with ultra high purity nitrogen and the benzene was transferred into the reactor. The agitator speed was set to 500 rpm and the reactor was allowed to equilibrate for 1 hour. After the one-hour benzene stir time had elapsed, 39.4 g ethylene was introduced into the reactor. A 31887 kPa-a (300 psig) nitrogen source was maintained connected to propylene vessel and open to the reactor during the entire experiment to maintain constant reaction pressure during the test. Liquid samples were taken at 30, 60, 120, 150, 180 and 240 min after addition of the ethylene.

Cumene Fixed Bed Test Procedure

All experiments were conducted in a fixed-bed, 3/8" or 3/4" OD tubular reactor in a downflow configuration. The reactor furnace was controlled in isothermal mode. The catalyst was dried off-line at 260° C. in air for two hours before loading. Experiments were conducted with catalyst as whole extrudates loaded into the 3/8" reactor. The catalyst bed was axially centered in the middle furnace zone. The catalyst was used extrudate form or crushed and sized to 50-60 mesh depending on the type of experiment. All catalysts were packed with inert sand to fill the interstitial void spaces. Reaction conditions were 125° C., benzene:propylene molar ratio of 2.8, and 31887 kPa-a (300 psig). Weight Hourly Space Velocity was adjusted during the experiments and ranged from 1 $h^{-1}$ WHSV (propylene basis) to 320 $h^{-1}$ WHSV (propylene basis).

At unit start-up, the reactor was brought to reaction pressure 31887 kPa-a (300 psig) with nitrogen, and heated to reaction temperature (125° C.) before introducing feed. The catalyst was typically allowed to equilibrate for one to two days to achieve steady state before data was collected.

Catalyst Preparation and Characterization

A MCM-49 catalyst were prepared by extruding a mixture of 80 wt. % MCM-49 crystal and 20 wt. % alumina into solid quadrulobe extrudates having a diameter of 1/20 inch and a length of 1/4 inch quadrulobe (hereinafter "MCM-49 1/20 inch Q catalyst"). The resultant catalyst particles had a surface to volume ratio of 198. A 50-60 mesh MCM-49 catalyst (hereinafter "MCM-49 50-60 mesh catalyst") was prepared by crush the 1/20 inch quadrulobe MCM-49 catalyst. The 50-60 mesh MCM-49 catalyst particles had a surface to volume ratio of 610.

A MCM-22 catalyst were prepared by extruding a mixture of 80 wt. % MCM-22 crystal and 20 wt. % alumina into solid cylindrical extrudates having a diameter of 1/16 inch and a length of 1/4 inch cylinder (hereinafter "MCM-22 1/16 inch C catalyst"). The resultant MCM-22 cylinder catalyst particles had a surface to volume ratio of 88. A 50-60 mesh MCM-22 catalyst (hereinafter "MCM-22 50-60 mesh catalyst") was prepared by crush the 1/16 inch cylinder MCM-22 catalyst. The 50-60 mesh MCM-22 catalyst particles had a surface to volume ratio of 610.

A zeolite beta catalyst were prepared by extruding a mixture of 80 wt. % zeolite Beta crystal and 20 wt. % alumina into solid cylindrical extrudates having a diameter of 1/16 inch and a length of 1/4 inch cylinder (hereinafter "zeolite beta 1/16 inch C catalyst"). The resultant zeolite beta cylinder catalyst particles had a surface to volume ratio of 88. A 50-60 mesh zeolite beta catalyst (hereinafter "zeolite beta 50-60 mesh catalyst") was prepared by crush the 1/16 inch cylinder zeolite Beta catalyst. The 50-60 mesh zeolite Beta catalyst particles had a surface to volume ratio of 610.

The three spray dried MCM-49 catalysts (sample A, sample B, and sample C) were produced by combining H-form zeolite crystal with water and binder according to the following procedure.

A slurry containing 20-25 wt. % solid was prepared according to this procedure: (A) adding aluminum chlorohydrate solution (ACH, from Reheis Inc., Berkeley Heights, N.J.) to deionized water and mixed at 700 RPM for 10 minutes using a Yamato Model 2100 homogenizer (Yamato Scientific America Inc., Orangeburg, N.Y.); (B) adding molecular sieve (MCM-49) to the solution from step (A) and mixed at 700 RPM for 10 minutes using the Yamato homogenizer Model 2100 used in step (A); (C) adding de-ionized water to make the slurry less viscous and milling the slurry at 6000 RPM using a Silverson 4LRT high-shear mixer (Silverson Machinery Inc., East Longmeadow, Mass.); (D) adding Versal 300 alumina (UOP LLP, Des Plaines, Ill.) while under mixing at 700 RPM using the Yamato Model 2100 homogenizer; (E) passing the slurry from step (D) through an in-line high-shear mixer at 7500 RPM (Silverson Machinery Inc., East Longmeadow, Mass.), the slurry produced had a pH of 3.2 measured at 23° C. This slurry now contains about 22 wt. % solids, of which 80 wt. % being molecular sieve MCM-49, 10 wt. % alumina derived from ACH, and 10 wt. % alumina derived from Versal 300. It was used for spray dry to produce a spray dried catalyst.

Spray dry of the above slurry was conducted using a Yamato DL-41 spray dryer (Yamato Scientific America, Orangeburg, N.Y.). An amount of 626.1 g of the slurry was spray dried. The spray dryer operated in a down spray mode using an atomization nozzle of 1 mm. The spray drying conditions are: feed rate: 36-40 g/min; inlet temperature: 350° C.; atomization pressure: 132 kPa-a; carrier gas (nitrogen) flow at 60% of full setting. Spray dry products were collected in a cyclone.

While the calculation of cylinder geometry is well known, the calculation of the quadrulobe geometry is more complex. The equations below detailed the calculations involved in determining the SAN of the quadrulobe materials.

| | |
|---|---|
| Perimeter (P) | $6\pi r$ |
| Cross Sectional Area (AX) | $(16 + \pi)r^2$ |
| Particle Surface Area ($SA_i$) | $SA_i = 2A_{xi} + P_i L$ |
| Volume (Vi) | $V_i = A_{xi} L$ |
| SA/V | $SA/V = \Sigma SA_i / \Sigma V_i$ |

Surface Area/Volume ratios were calculated for the quadrulobe and cylinder extrudates and for the 50-60 mesh particles by approximating the particles as cylinders with a 0.25 mm diameter and 0.25 mm length. The following table below listed SAN ratios for the particle sizes tested.

| Name | 1/20 inch Quadrulobe | 1/16 inch Cylinder | 50-60 mesh particle |
|---|---|---|---|
| Geometry | Quadrulobe | Cylinder | Particle |
| Diameter | 1/20 inch* | 1/16 inch | 1/100 inch |
| Length | 1/4 inch | 1/4 inch | 1/100 inch |
| SA/V ($in^{-1}$) | 198 | 88 | 610 |
| SA/V ($cm^{-1}$) | 78 | 35 | 241 |

*Diameter was measured across the minimum.

The particle sizes and SAN ratios of samples A-C were measured and listed in the following table:

| | Samples | | |
|---|---|---|---|
| | A | B | C |
| Particle size | 21 μm | 25 μm | 14 μm |
| SA/V ($in^{-1}$) | 7257 | 6096 | 10886 |
| SA/V ($cm^{-1}$) | 2867 | 2408 | 4300 |

The MCM-49 1/20 inch Q catalyst, the MCM-49 50-60 mesh catalyst, the MCM-49 sample A, the MCM-49 sample B, the MCM-49 sample C, the MCM-22 1/16 inch C catalyst, and the MCM-22 50-60 mesh catalyst were tested according the cumene batch test procedure.

The MCM-49 1/20 inch Q catalyst, the MCM-49 50-60 mesh catalyst, the zeolite beta 1/16 inch C catalyst, and the zeolite beta 50-60 mesh catalyst were tested according the cumene fix-bed test procedure.

The MCM-49 1/20 inch Q catalyst and the MCM-49 50-60 mesh catalyst were tested according the ethylbenzene batch test procedure.

The catalyst selectivity was measured by the weight ratio of di-isopropylbenzene over cumene or the weight ratio of di-ethylbenzene over ethylbenzene. The ratios were normalized to extrudates as shown.

The following table summarizes the results.

| Catalyst | Normalized DIPB/IPB or DIEB/EB (%) | DIPB/IPB or DIEB/EB reduction (%) |
|---|---|---|
| MCM-49 catalysts tested with cumene batch test procedure | | |
| MCM-49 1/20 inch Q | 100% | |
| MCM-49 50-60 mesh | 70% | 30% |
| MCM-49 Sample A | 66% | 34% |
| MCM-49 Sample B | 77% | 23% |
| MCM-49 Sample C | 91% | 9% |
| MCM-22 catalysts tested with cumene batch test procedure | | |
| MCM-22 1/16 inch C | 100% | |
| MCM-22 50-60 mesh | 87% | 13% |
| MCM-49 catalysts tested with cumene fix-bed test procedure | | |
| MCM-49 1/20 inch Q | 100% | |
| MCM-49 50-60 mesh | 46% | 54% |
| Zeolite beta catalysts tested with cumene fix-bed test procedure | | |
| MCM-49 1/20 inch Q | 100% | |
| MCM-49 50-60 mesh | 58% | 42% |
| MCM-49 catalysts tested with ethylbenzene batch test procedure | | |
| MCM-49 1/20 inch Q | 100% | |
| MCM-49 50-60 mesh | 77% | 23% |

As results clearly shown, for both ethylbenzene and Cumene synthesis, an increase in SAN (greater than 79 $cm^{-1}$)

results in substantial decreases in DIPB/IPB ratio, resulting in a more selective to the desired product ethylbenzene or isopropylbenzene (cumene) and economically attractive process.

All patents, patent applications, test procedures, priority documents, articles, publications, manuals, and other documents cited herein are fully incorporated by reference to the extent such disclosure is not inconsistent with this disclosure and for all jurisdictions in which such incorporation is permitted.

When numerical lower limits and numerical upper limits are listed herein, ranges from any lower limit to any upper limit are contemplated.

While the illustrative embodiments of the disclosure have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the disclosure pertains.

What is claimed is:

1. A process for producing a monoalkylated aromatic compound in an alkylation reaction zone, said process comprising the steps of:
    (a) providing a first catalytic particulate material which comprises MCM-56 and an alumina binder, said first catalytic particulate material sized 50-60 mesh and having a ratio of surface area over volume ratio in the range of 241 to 2867 $cm^{-1}$;
    (b) providing said alkylation reaction zone with an alkylatable aromatic compound, an alkylating agent, and said first catalytic particulate material; and
    (c) contacting said alkylatable aromatic compound and said alkylating agent with said catalytic particulate material in said alkylation reaction zone maintained under alkylation conditions, to form a product comprised of said monoalkylated aromatic compound and polyalkylated aromatic compound(s);
    whereby the molar ratio of said polyalkylated aromatic compound(s) over said monoalkylated aromatic compound produced by said first catalytic particulate material is less than the molar ratio of polyalkylated aromatic compound(s) over monoalkylated aromatic compound produced by a second catalytic particulate material and said alkylation reaction zone is operated under the same alkylation conditions,
    wherein at least 51 wt. % of said second catalytic particulate material having a ratio of surface area over volume between 78 and 79 $cm^{-1}$.

2. The process of claim 1, wherein the moles of said monoalkylated aromatic compound produced by said first catalytic particulate material is greater than the moles of monoalkylated aromatic compound produced by said second catalytic particulate material when said alkylation reaction zone is operated under the same alkylation conditions for the same amount of time with the same mass of said first and second catalytic particulate material,
    wherein at least 51 wt. % of said second catalytic particulate material having a ratio of surface area over volume between 78 and 79 $cm^{-1}$.

3. The process recited in claim 1, wherein the moles of said monoalkylated aromatic compound in said product is increased as compared to the moles of said monoalkylated aromatic compound produced by said second catalytic particulate material when at least 51 wt. % of said second catalytic particulate material has a surface area over volume ratio between 78 and 79 $cm^{-1}$ and said alkylation reaction zone is operated under the same alkylation conditions for the same amount of time with the same mass of catalytic particulate material.

4. The process of claim 1, wherein said first catalytic particulate material is made by a process selected from the group consisting of spray drying, crushing, chopping, extrusion, and sieving.

5. The process of claim 1, wherein said first and second catalytic particulate material comprises a molecular sieve having a channel size greater than 5 Å.

6. The process of claim 1, wherein said alkylation conditions include a temperature from about 20° C. to about 500° C., a pressure from about 20.3 to 4800 kPa-a, a WHSV from about 0.1 to about 50 $h^{-1}$ based on the weight of said alkylating agent, and a molar ratio of said alkylatable compound over said alkylating agent from about 0.1:1 to 50:1.

7. The process of claim 1, wherein said monoalkylated aromatic compound comprises ethylbenzene, said alkylatable aromatic compound comprises benzene and said alkylating agent comprises ethylene.

8. The process of claim 1, wherein said monoalkylated aromatic compound comprises cumene, said alkylatable aromatic compound comprises benzene and said alkylating agent comprises propylene.

9. The process of claim 1, wherein said monoalkylated aromatic compound comprises sec-butyl-benzene, said alkylatable aromatic compound comprises benzene and said alkylating agent comprises butene.

10. The process of claim 1, wherein said product comprises polyalkylated aromatic compound(s), further comprising steps of:
    (d) separating said polyalkylated aromatic compound(s) from said product to form a transalkylation feed stream; and
    (e) contacting at least a portion of said transalkylation feed stream with a feedstock comprising an alkylatable aromatic compound in the presence of a transalkylation catalyst to produce a transalkylation effluent in a transalkylation reaction zone maintained under transalkylation conditions, said transalkylation effluent which comprises said monoalkylated aromatic compound.

11. The process of claim 10, wherein said transalkylation catalyst comprises a molecular sieve selected from the group consisting of MCM-22, MCM-36, MCM-49 and MCM-56, beta zeolite, faujasite, mordenite, TEA-mordenite, PSH-3, SSZ-25, ERB-1, ITQ-1, ITQ-2, zeolite Y, Ultrastable Y (USY), Dealuminized Y, rare earth exchanged Y (REY), ZSM-3, ZSM-4, ZSM-18, ZSM-20, or any combination thereof.

12. The process of claim 1, wherein said transalkylation conditions include a temperature of 100 to 300° C. and a pressure of 696 to 4137 kPa-a, a WHSV based on the weight of said polyalkylated aromatic compound(s) of about 0.5 to 200 $h^{-1}$, a molar ratio of said alkylatable aromatic compound to said polyalkylated aromatic compound(s) of 0.5:1 to 10:1.

13. The process of claim 1, further comprising the step of adapting an existing vapor, liquid, or mixed phase alkylation reaction zone of an ethylbenzene or cumene plant to form said product.

* * * * *